United States Patent
Peled

(10) Patent No.: US 11,890,487 B2
(45) Date of Patent: Feb. 6, 2024

(54) METHOD AND APPARATUS FOR MULTI-CHANNEL SIMULTANEOUSLY HIGH POWER MAGNETIC COIL DRIVER

(71) Applicant: Yona Peled, Kiryat Tiv'on (IL)

(72) Inventor: Yona Peled, Kiryat Tiv'on (IL)

( * ) Notice: Subject to any disclaimer, the term of this patent is extended or adjusted under 35 U.S.C. 154(b) by 0 days.

(21) Appl. No.: 17/276,504

(22) PCT Filed: Sep. 26, 2019

(86) PCT No.: PCT/IL2019/051062
§ 371 (c)(1),
(2) Date: Mar. 16, 2021

(87) PCT Pub. No.: WO2020/065651
PCT Pub. Date: Apr. 2, 2020

(65) Prior Publication Data
US 2021/0268300 A1 Sep. 2, 2021

Related U.S. Application Data

(60) Provisional application No. 62/737,136, filed on Sep. 27, 2018.

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
CPC ................................. A61N 2/006; A61N 2/02
See application file for complete search history.

(56) References Cited

U.S. PATENT DOCUMENTS

| | | |
|---|---|---|
| 2004/0078056 A1 | 4/2004 | Zangen et al. |
| 2006/0287566 A1 | 12/2006 | Zangen et al. |
| 2009/0156884 A1 | 6/2009 | Schneider et al. |
| 2010/0185042 A1 | 7/2010 | Schneider et al. |
| 2010/0256438 A1 | 10/2010 | Mishelevich et al. |
| 2011/0213194 A1* | 9/2011 | Fischell ............ A61N 2/02 600/14 |
| 2011/0319700 A1 | 12/2011 | Schneider |
| 2014/0243941 A1* | 8/2014 | Rogers ............ A61F 7/12 607/113 |

FOREIGN PATENT DOCUMENTS

| | | | |
|---|---|---|---|
| WO | 2008005386 A2 | 1/2008 | |
| WO | WO-2018185369 A1 * | 10/2018 | ............ A61N 2/006 |

OTHER PUBLICATIONS

International Search Report issued in Application No. PCT/IL2019/051062 dated Jan. 9, 2020, 15 pages.
Written Opinion issued in Application No. PCT/IL2019/051062 dated Jan. 9, 2020, 4 pages.
(Continued)

*Primary Examiner* — Christine H Matthews
(74) *Attorney, Agent, or Firm* — CANTOR COLBURN LLP

(57) ABSTRACT

An apparatus for a multi-channel high power magnetic coil driver, comprising: a plurality of magnetic coil drive modules, each of which is connected to a magnetic coil that is adapted to produce a magnetic field in a controlled manner.

12 Claims, 16 Drawing Sheets

(56) References Cited

OTHER PUBLICATIONS

Extended European Search Report for European Patent Application No. 19865818.9, Filing Date Sep. 26, 2019, dated May 30, 2022; 8 pages.
Kai-Hsiung Hsu et al: "A 3-D Differential Coil Design for Localized Magnetic Stimulation", IEEE Transactions on Biomedical Engineering, IEEE, USA, vol. 48, No. 10, Oct. 1, 2001, XP011007147.

* cited by examiner

METHOD AND APPARATUS FOR MULTI-CHANNEL SIMULTANEOUSLY HIGH POWER MAGNETIC COIL DRIVER

CROSS-REFERENCE TO RELATED APPLICATIONS

This Application is a U.S. National Stage Application of PCT/IL2019/051062 filed Sep. 26, 2019, which claims benefit of U.S. Provisional Application No. 62/737,136 filed on Sep. 27, 2018, both of which are incorporated by reference in their entirety herein.

FIELD OF THE INVENTION

The present invention relates to the field of high power magnetic coil systems. More particularly, the invention relates to a method and apparatus for producing high power magnetic fields that can be applied to, for example, a human body for therapy.

BACKGROUND OF THE INVENTION

A multi-channel deep Transcranial Magnetic Stimulations (TMS) brain stimulation apparatus provides a multiplicity of stimulation channels through which stimulation may be delivered simultaneously deep within the brain of the patient, each channel may have different parameters which allows the magnetic focal point (the maximum point of the magnetic field) to move to any three-dimensional (3D) point in the volume of the patient brain in case of use 3 channels with coils on the X, Y and Z axis located around the patient's head.

Multi-channel deep TMS brain stimulation or high frequency deep brain stimulation (DBS), with simultaneously controlled output magnetic pulses, will be able to produce 3D magnetic focal point energy in a given volume such as the human brain, and with the ability to reach almost each point in the volume of the brain.

Multi-channel deep TMS brain stimulation will allow the physicians to invent new brain treatments that were not able till now, or replace invasive treatments with non-invasive treatments.

Sport injury and broken bones wound healing that will have the ability to reach the target on broken bones with high accuracy in 3D volume, and will help to treat the bone tissue healing, and may use for health magnetic therapy for spine injury.

Multi-channel magnetic coil drivers will allow development of a new line of impact wave treatment systems and a new method of treatments that may use them.

Multi-channel magnetic coil drivers will allow multi-stations of wireless charging for wearable battery operated for consumer electronics, wearables, handheld computers, smartwatches, fitness trackers, hearing aids, earphones, sporting goods, medical devices, high power electrical car wireless charging and other devices.

Multi-channel magnetic coil drivers will allow anti-gravity plate solutions for transportations such as train and tracks, or all other use that need controlled magnetic fields.

It is an object of the present invention to provide a system which is capable of providing multi-channel magnetic coil drivers that enable new directions on apparatus and methods that will be based on such drivers.

Other objects and advantages of the invention will become apparent as the description proceeds.

SUMMARY OF THE INVENTION

An apparatus for a multi-channel high power magnetic coil driver, comprising: a plurality of magnetic coil drive modules, each of which is connected to a magnetic coil that is adapted to produce a magnetic field in a controlled manner.

According to an embodiment of the invention, each channel of the magnetic coil driver is adapted to work simultaneously at the same time controlled from a main control, while enabling each of the magnetic coil driver channels to get different set of parameters, thus each magnetic coil driver channel can deliver different output magnetic energy.

According to an embodiment of the invention, each magnetic coil drive module is being powered by a capacitor bank.

According to an embodiment of the invention, one or more capacitors are being charged by a charger that is being fed by mains, by a battery, by a renewable energy source, or any combination thereof.

According to an embodiment of the invention, each magnetic coil is assembled from one magnetic coil or plural of magnetic coils that connected in serial and/or parallel combinations.

According to an embodiment of the invention, the magnetic coil is selected from the group consisting of an Air Coil, Tesla Coil, or any other type of coils that can be connected in serial or parallel or a combination of both.

According to an embodiment of the invention, outputs currents and voltage of each magnetic coil driver channel, is sampled and send to a main controller as a monitoring feedback.

According to an embodiment of the invention, a signal of a magnetic stimulation as applied by the magnetic coils is assumed to be a solution of an ordinary differential equation including a self-oscillating system with a stable limit cycle.

According to an embodiment of the invention, each magnetic pulse can change values (by the main controller) as a result of feedback received from a previous magnetic pulse, thereby enabling the output of a multi-channel high power magnetic coil driver to act as a regulated output that delivers magnetic energy that is controlled by feedback. Each magnetic coil drive module outputs current and voltage. Controlling the current and voltage levels of the output of each magnetic coil drive module is done by changing an initial (start) condition of the differential equation by a change of a controlled voltage that charges a resonant capacitor of each magnetic coil drive module before each produced magnetic pulse.

According to an embodiment of the invention, further comprises an end-of-charge mechanism configured for stopping the wireless charging when a target charge voltage is achieved.

DETAILED DESCRIPTION OF THE INVENTION

Figure 1:
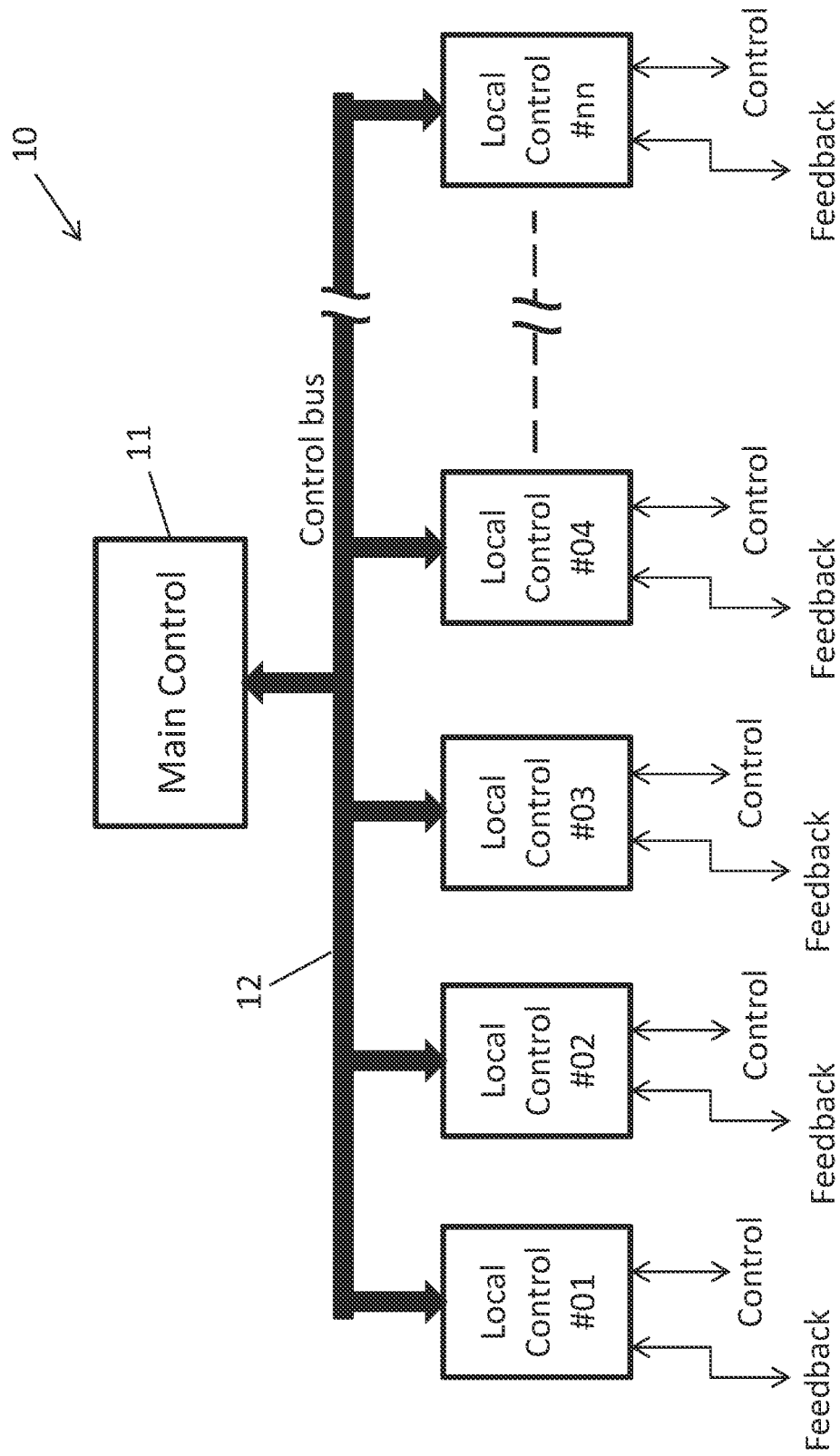
FIG. 1 is a general control block diagram, in which each magnetic drive module has its local control, according to an embodiment of the invention.

This invention generally relates to an apparatus with multi-channels of high power magnetic coil drive modules, that include from one channel to plural channels of magnetic coil drive modules, and each magnetic coil drive module include its magnetic coil that may be assembled from one magnetic coil or plural of magnetic coils that connected in serial and/or parallel combinations.

This invention generally relates to a method for producing high power magnetic fields using magnetic coil drive modules and its magnetic coil.

According to an embodiment of the present invention, power source for the apparatus will be from mains, generators, battery set, renew energy source or any other energy source.

Each channel of magnetic coil drive module will be sourced from the main power reservoir (Main Capacitor Bank) or from plural energy sources that will charge its local power reservoir (Local Capacitor Bank).

Each magnetic coil driver channel output will be connected to a coil that produced the magnetic field.

All magnetic coil driver channels will work simultaneously at the same time controlled from main controller, but each of the magnetic coil driver channels may get different set of parameters, which mean that each magnetic coil driver channels may deliver different output magnetic energy.

According to an embodiment of the invention, each magnetic coil driver channel may work with different parameters simultaneously.

Each magnetic coil driver channel may work on a different frequency, and with a different current output parameter setting, means that also with a different magnetic field per channel magnetic coil.

According to an embodiment of the invention, all magnetic coil driver channels may be connected to its one magnetic coil combined on its output or to plural magnetic coils on its outputs or combinations of single and plural magnetic coils on its output.

According to an embodiment of the invention, the magnetic coil may be an Air Coil, Tesla Coil, or any type of coils that may be connected in serial or parallel or a combination of both.

The outputs currents and voltage for each magnetic coil driver channel, will be sampled and send to the main controller as a monitoring feedback.

The signal of the magnetic stimulation is assumed to be a solution of an ordinary differential equation including a self-oscillating system with stable limit cycle.

Method of controlling the output self-oscillating current and the magnetic field by changing the start condition of the differential equation, meaning the change of controlled voltage that charge the high voltage capacitors on the self-oscillating circuit before each pulse, results in influencing the output current and magnetic field of each specific channel of the magnetic coil drive module.

Reference will now be made to several embodiments of the present invention, examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

The following discussions are intended to provide a brief, general description of suitable multi-channel system configurations in which the invention may be implemented. While the invention will be described in the general context of magnetic coil drive modules that operate in conjunction with capacitors, coils and switches, those skilled in the art will recognize that the invention may also be implemented in combination with other magnetic coil drive modules.

FIG. 1 schematically illustrates a general control block diagram 10, according to an embodiment of the invention. General control block diagram comprises a main control 11 and a plurality of local controllers as indicated by #01, #02, #03, #04 to #nn, each of which adapted to control a corresponding magnetic coil drive module.

Main control 11 and the local controllers may communicate via a control bus 12. In addition, sampled outputs currents and voltage of each magnetic coil driver module, are provided to the main controller as a monitoring feedback that is received by each local control.

Figure 2:
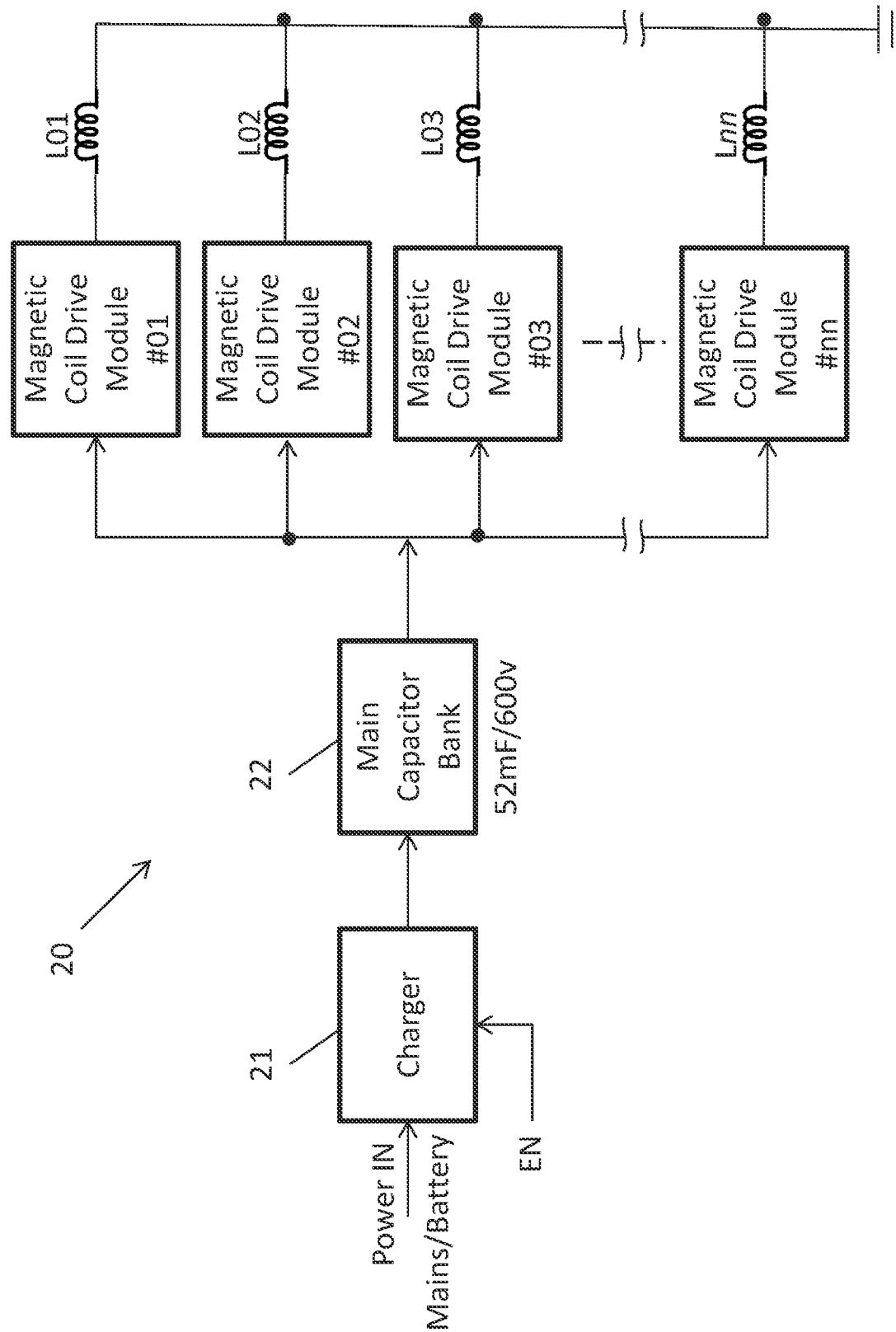
FIG. 2 schematically illustrates one charger and plural magnetic drive modules, wherein each one with his coil, according to an embodiment of the invention.

FIG. 2 schematically illustrates a multi-channel system 20 for producing high power magnetic fields with a single charger and a plurality of magnetic coil drive modules, according to an embodiment of the invention. Configuration 20 comprises a charger 21, main capacitor bank (MCB) 22 and a plurality of magnetic coil drive modules (as indicated by #01, #02, #03 to #nn), wherein each magnetic coil drive module comprises a corresponding coil (as indicated by L01, L02, L03 to Lnn). Charger 21 is configured to charge MCB 22 and it can be fed by power supplied from the mains or from a suitable battery. Charger 21 may comprise an enabler (as indicated by EN) that is adapted to connect/disconnect the charger 21 from the supplied power. MCB 22 is configured to supply voltage suitable to each magnetic coil drive module. For example, MCB 22 may output 560 Volt from capacitors of 52 mF/600V.

Figure 3:
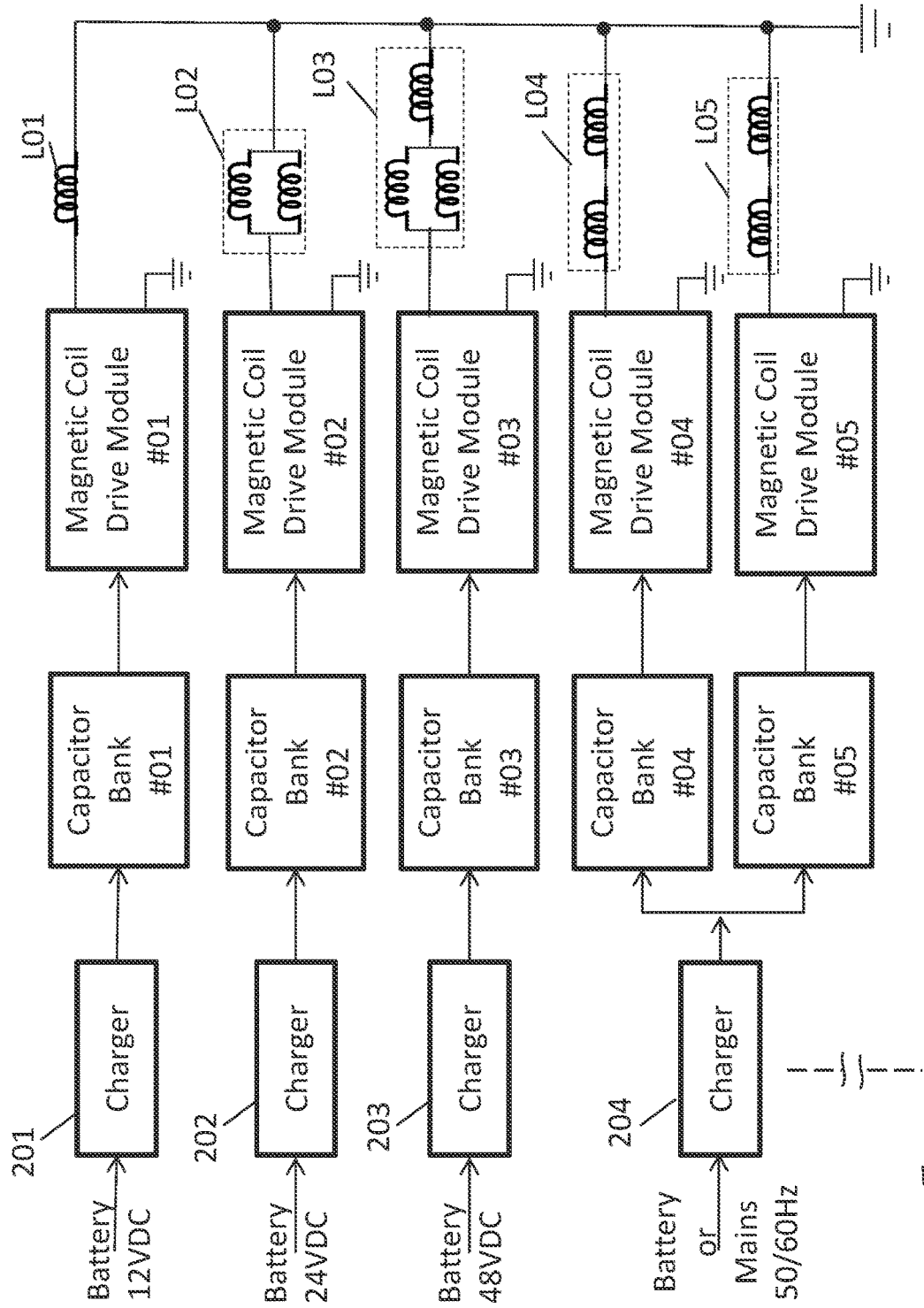
FIG. 3 Plural schematically illustrates Chargers and plural Magnetic Drive Modules, different Coil combination, according to an embodiment of the invention.

FIG. 3 schematically illustrates an example of a multi-channel system 30 for producing high power magnetic fields, according to an embodiment of the invention. System 30 comprises a plurality of chargers 201, 202, 203 and 204, a plurality of capacitor banks (CB) #01, #02, #03, #04 and #05 and a plurality of magnetic coil drive modules #01-#05 with different coil combination L01-L05. System 30 demonstrates some possible system design configurations, as follows:

Charger 201 charges CB #01 and is being fed by a 12 Vdc battery. CB #01 supplies power to magnetic coil drive module #01 that is configured to drive coil L01;

Charger 202 charges CB #02 and is being fed by a 24 Vdc battery. CB #02 supplies power to magnetic coil drive module #02 that is configured to drive coil L02. In this example, coil L02 is comprised of two parallel coils;

Charger 203 charges CB #03 and is being fed by a 48 Vdc battery. CB #03 supplies power to magnetic coil drive module #03 that is configured to drive coil L03. In this example, coil L03 combines two parallel coils in serial with a third coil; and Charger 204 simultaneously charges CB #04 and CB #05 and it can be fed by a battery or the mains (50/60 Hz). In this configuration, CB #04 supplies power to magnetic coil drive module #04 that is configured to drive coil L04, and CB #05 supplies power to magnetic coil drive module #05 that is configured to drive coil L05. In this example, coil L04 and coil 05 each comprised of two coils in serial.

System 30 shows an example of possible configurations and combinations of elements such as chargers, capacitor banks, magnetic coil drive modules and coils. However, as will be appreciated by a person skilled in the art, other multi-channel system designs that include different configurations and combinations of such elements can be used in accordance with requirements of each specific application for producing high power magnetic fields. For example, a multi-channel system applying magnetic field to a human body for therapy electromagnetic coil pulsating field.

Figure 4:
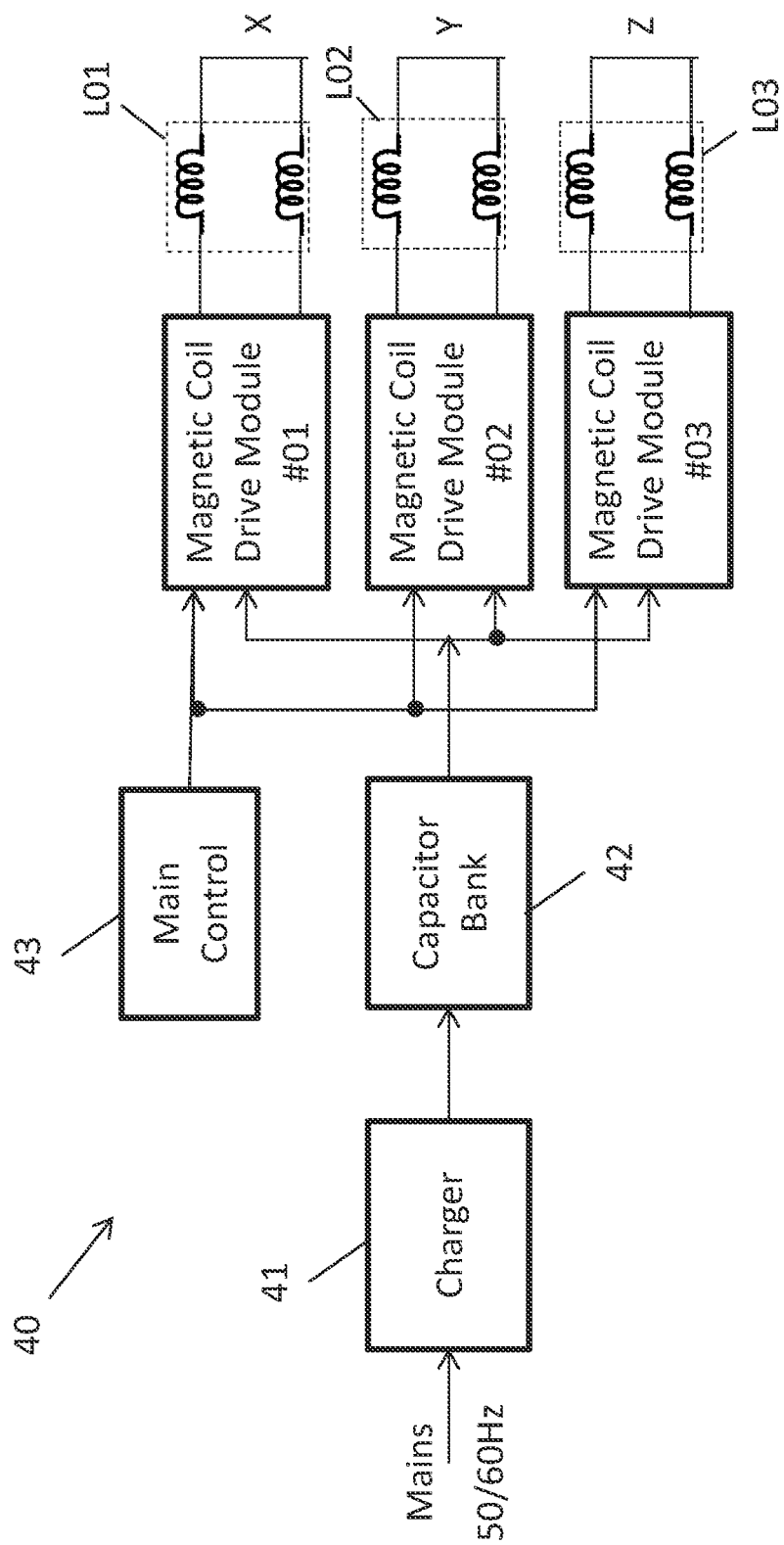
FIG. 4 schematically illustrates three magnetic drive modules, with X, Y and Z axis Coil combination, according to an embodiment of the invention.

FIG. 4 schematically illustrates a multi-channel system 40 for simultaneously producing controlled output magnetic pulses, according to an embodiment of the invention. System 40 comprises three magnetic coil drive modules #01-#03, with X, Y and Z axis coil combination as indicated by coils L01-L03. In this configuration, each of the coils L01-L03 is comprised of two serial "floating" isolated coils (i.e., non-grounded coils). A CB 42 is configured to supply power to the three magnetic coil drive modules #01-#03, and a charger 41 is adapted to charge CB 42 from power supplied by the mains. A main controller 43 is configured to control the three magnetic coil drive modules #01-#03 as well as to receive monitoring feedback from the output of each magnetic coil drive module (i.e., from X, Y and Z axis), in a similar manner as described with respect to FIG. 1 hereinabove. Due to the monitoring feedback each charging pulse can be controlled, i.e., the voltage can be adjusted as well as other parameters between pulses. By control the charge time of high-voltage output capacitor it will be charge to the pre-desired voltage value, charge time controlled by a switching timing control (e.g., IGBT switch such as indicated by SW1 in FIG. 10).

The simultaneously controlled output magnetic pulses at the X, Y and Z axis of system 40 can be used for different application. For example, it can be used as part of a multi-channel deep TMS brain stimulation apparatus that provides a multiplicity of stimulation channels through which stimulation may be delivered simultaneously deep within the brain of the patient, each channel may have different parameters which allows the magnetic focal point to move to any 3D point in the volume of the patient brain in case of use 3 channels with coils on the X, Y and Z axis located around the patient's head.

Figure 5:
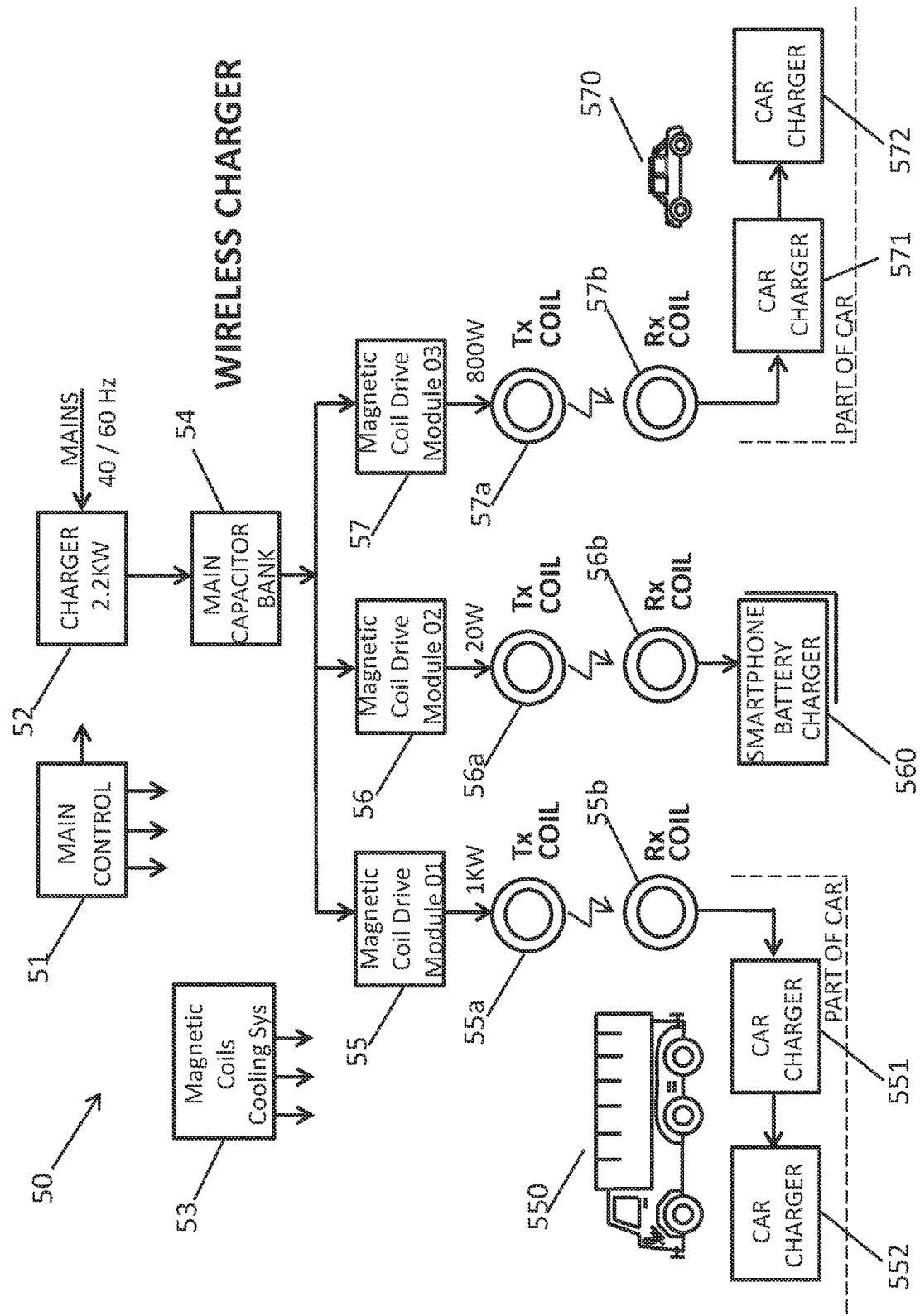
FIG. 5 schematically illustrates multi-channel magnetic drive for car and wearable devices wireless charging, according to an embodiment of the invention.

FIG. 5 schematically illustrates a multi-channel system 50 for simultaneously producing wireless charging, according to an embodiment of the invention. System 50 comprises a main controller 51, a charger 52 (e.g., 2.2 Kw), a MCB 54, a magnetic coils cooling system 53 and one or more magnetic coil drive modules 55-57. Each magnetic coil drive module comprises a transmitting coil (Tx coil) that is adapted to wirelessly produce controlled output magnetic pulses that are suitable to be received by a corresponding receiving coil (Rx coil), as indicated by numerals 55a-57a and numeral 55b-57b, respectively.

The receiving coils (Rx coils) can be implemented as part of a dedicated device or object such as part of a car, a smartphone, etc. for enabling a wireless charging of that object or device. For example, magnetic coil drive module 55 may produce 1 kw for high power applications such as wirelessly charging a car battery 552 of a truck 550 via a car charger 551. Similarly, magnetic coil drive module 57 may produce 800 w for high power applications such as simultaneously fast charging a battery of a vehicle in wireless manner, such as a battery of a car, an electric bicycle, an electric scooter and the like (e.g., a car battery 572 of a car 570 via a car charger 571). According to an embodiment of the invention, the system further comprises an end-of-charge mechanism configured for stopping the wireless charging when a target charge voltage is achieved. Magnetic coil drive module 56 may produce 10 w for relatively low power applications such as wirelessly fast charging a smartphone 560.

Figure 6:
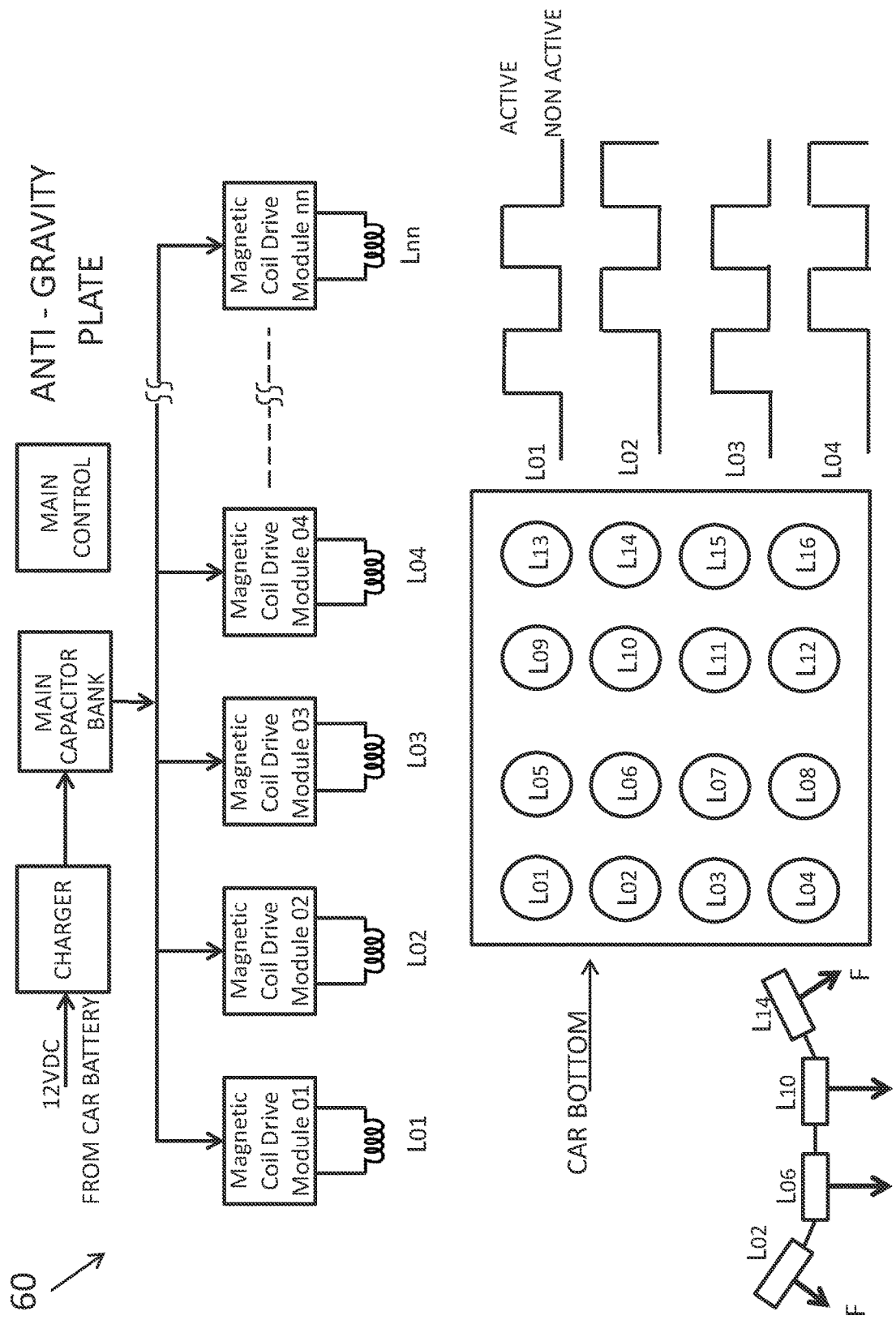
FIG. 6 schematically illustrates multi-channel magnetic drive for an anti-gravity platform, according to an embodiment of the invention.

FIG. 6 schematically illustrates a multi-channel system 60 for simultaneously producing controlled output magnetic pulses that forms an anti-gravity plate for a future vehicle or platform, according to an embodiment of the invention. System 60 comprises a charger that is powered by 12 Vdc from a battery, a MCB, a main control and a plurality of magnetic coil drive modules. In this embodiment, the coils are deployed at the bottom of the vehicle/platform in such a way that the magnetic pulses produce force vectors towards the surface beneath the vehicle/platform (e.g., towards the surface of a road). As indicated in the graphs section of FIG. 6, while some of the coils active (producing a pulse), at the same time the other coils are inactive (not producing a pulse). This alternating way of operation in combination with the formation of the coils and the force vectors they produce, results in the application of the anti-gravity platform. Coils assembled with an angle to the platform surface, can be used to produce power vectors that will allow a backward/forward movement of the platform, as indicated by coils L01-L04 and L13-L16. In order to enable a floating effect of the platform, the system will need to produce a magnetic field that considers the mass of the platform as well as the load that it may comprise.

Figure 7:
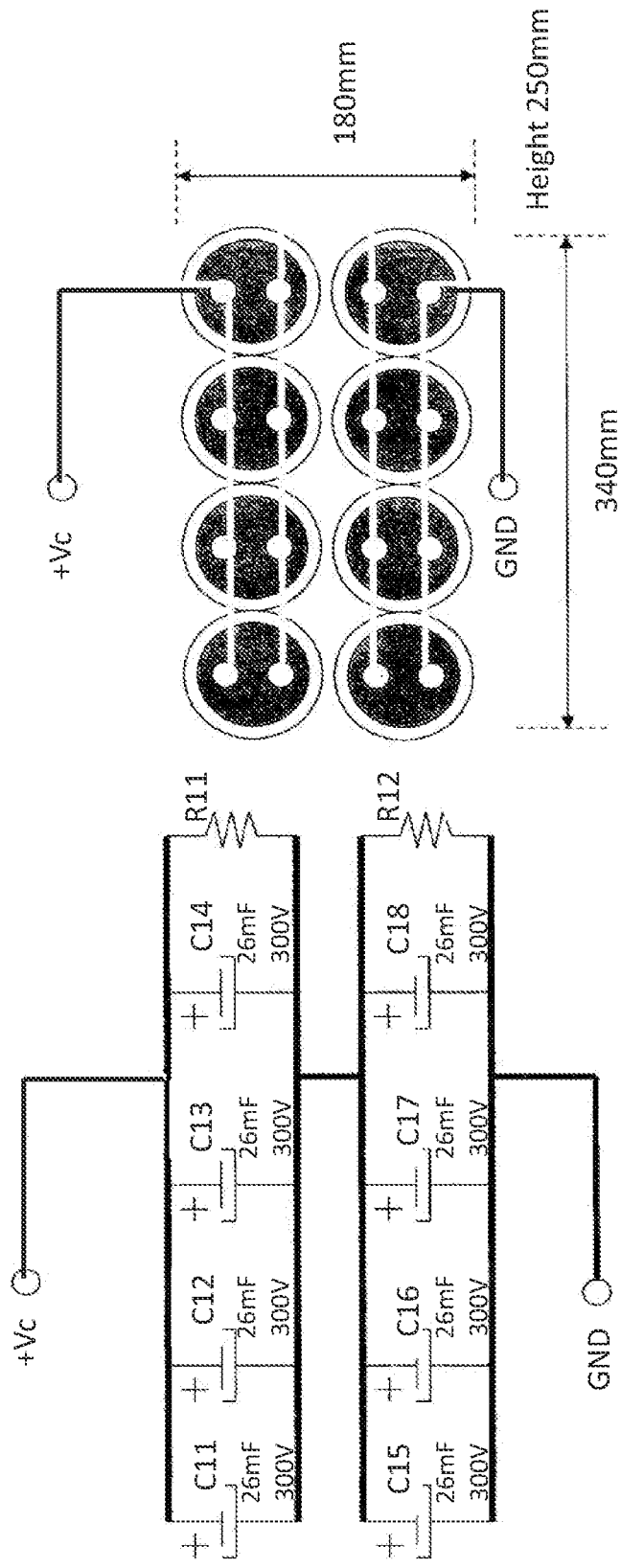
FIG. 7 schematically illustrates a main capacitor bank, according to an embodiment of the invention.

FIG. 7 schematically illustrates a main capacitors bank (MCB) that can be used in accordance with the multi-channel simultaneously high power magnetic coil driver of the present invention. The MCB comprises a plurality of capacitors C11-C18 having similar properties of 26 mF/300V that are arranged in two connected parallel groups that forms 52 mF/600V, the first group C11-C14 and the second group C15-C18, wherein each group comprises a resistor R11 and R12 (100 kohm/2 w), respectively. Such an arrangement of the MCB will allow achieving the desired maximum voltage and capacity of the MCB.

Figure 8:
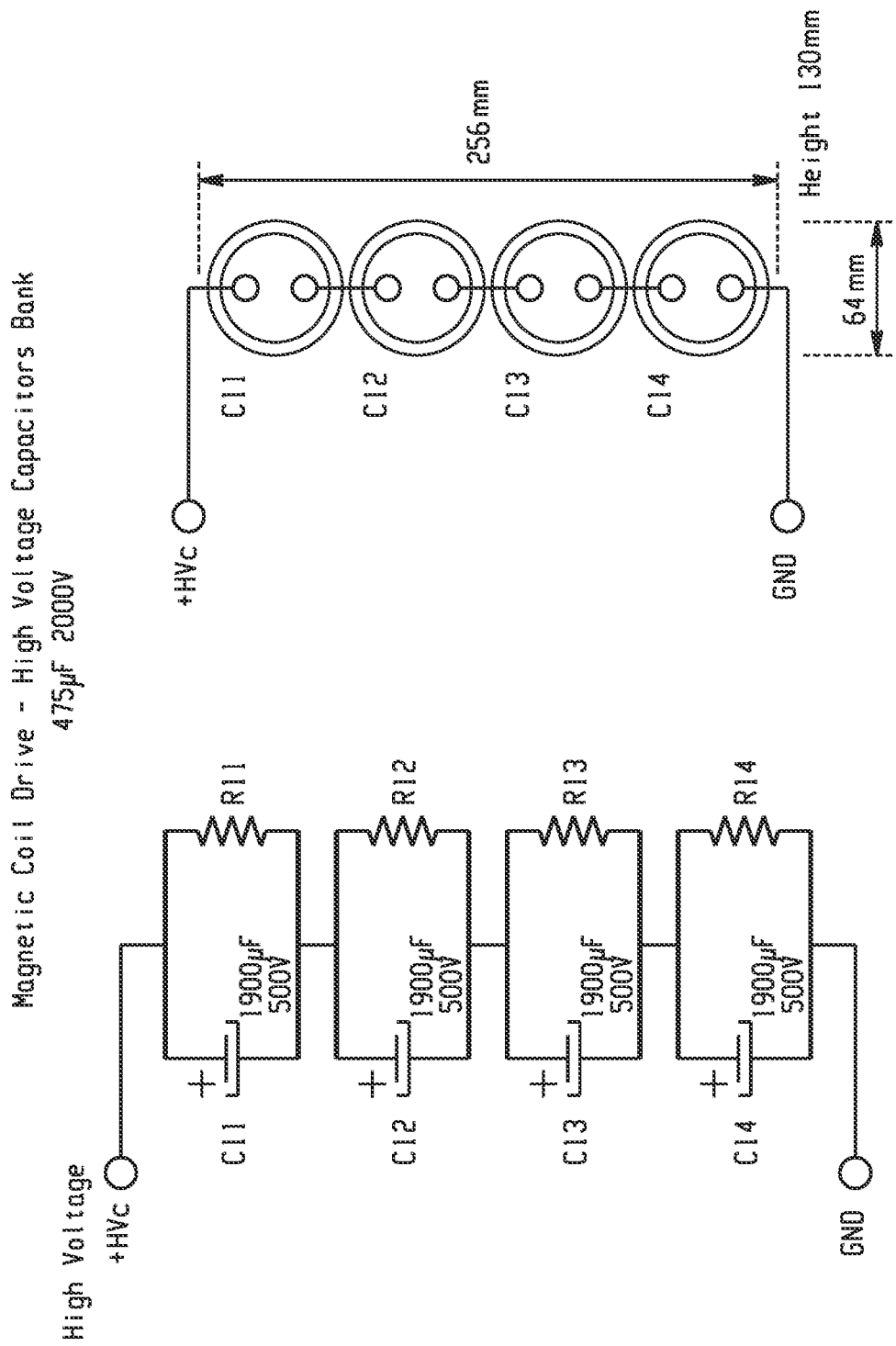
FIG. 8 schematically illustrates a part of a magnetic coil drive module that shows one of the optional channels of the high voltage capacitors bank, according to an embodiment of the invention.

FIG. 8 schematically illustrates a main high-voltage capacitors bank (MHCB) that can be used in accordance with the multi-channel simultaneously high power magnetic coil driver of the present invention. The MHCB comprises a plurality of capacitors C11-C14 having similar properties of 1900 µF/500V that are arranged in a way that forms 475 µF/2000V, wherein each capacitor is arranged in a parallel form with a resistor of 150 kohm/2 w, as indicated by R11-R14, respectively. Such an arrangement of the MHCB will allow achieving the desired maximum voltage and capacity of the MHCB. Each capacitor has its own high-voltage (HV) capacitor charger with separate charging voltage control, hence each HV capacitor unit may be charged to a different voltage value, wherein the output of the MHCB is the sum of the voltages of all the HV capacitor units (as shown in this figure, the HV capacitor bank is comprised of 4 HV capacitor units). In this example, the maximum possible output voltage is 2000V, which is the sum of all the 4 HV capacitor units (each HV capacitor unit is 500V maximum). In practice, in order to maintain HV capacitor long-life, each HV capacitor unit will be limited to 450V maximum (i.e., less than the actual maximum), thus in this case the maximum output voltage will be 1800V.

Figure 9:
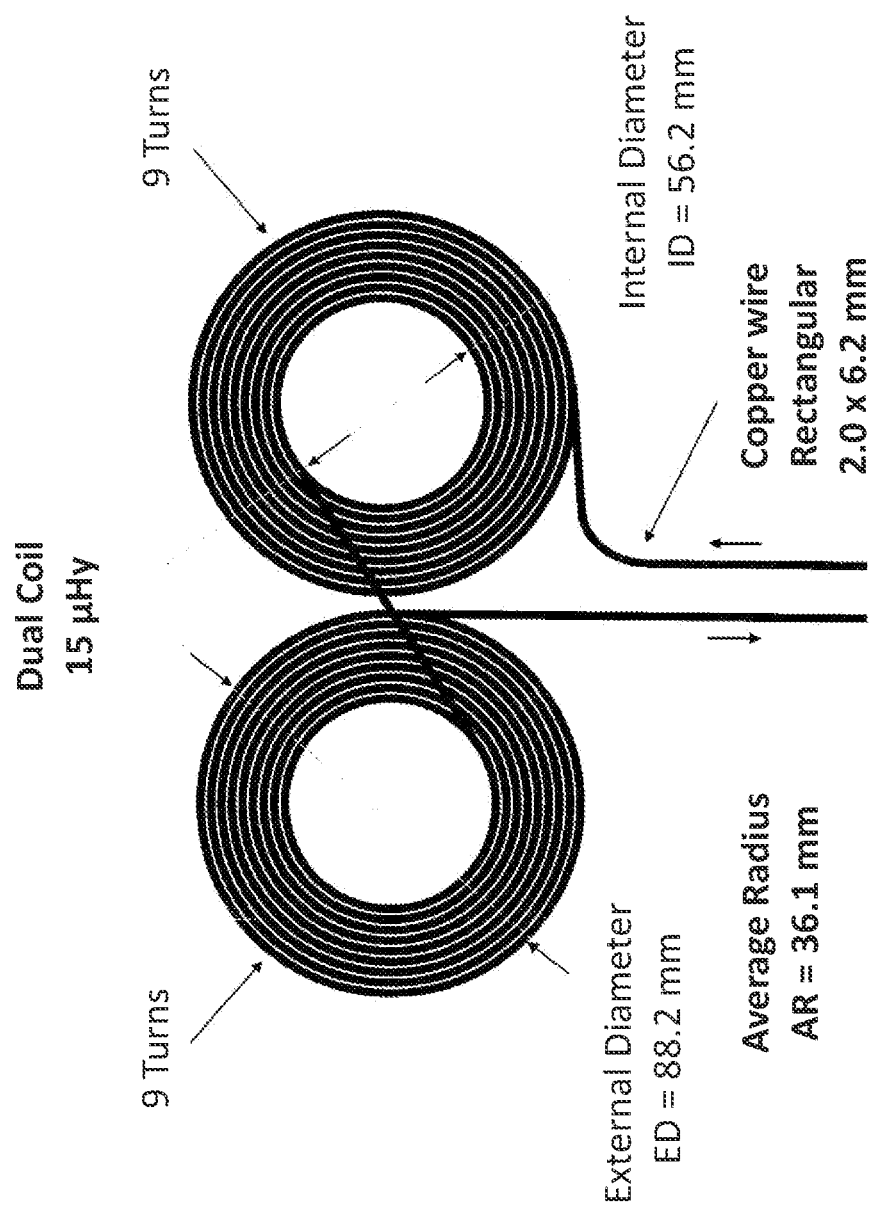
FIG. 9 schematically illustrates an example of a dual coil that can be used in conjunction with the magnetic coil drive module of the present invention.

FIG. 9 schematically shows a standard dual coil (e.g., as used in Deep TMS, such as D70 Alpha flat coil by Magstim®) that can be used as the coil at the output of each magnetic coil drive module of the present invention, through which the magnetic pulses are produced. For example, each coil is formed by 9 turns and it can be made of a single copper wire (e.g., 2.0×6.2 mm). In this embodiment, the dual coil is of 15 µHy, the internal dimension of each coil is about 56.2 mm and the external dimension is about 36.1 mm and the average radius is about 36.1 mm. As will be appreciated by a person skilled in the art, the coils may be a single coil, dual coils or any other combinations of coils. A coil may have any shape of closed-loop (round, square, triangle, or any other closed-loop shape).

Calculation of the coil magnetic field at distance from ring surface "r" can be obtain by applying standard mathematical equation for magnetic field of one loop, as well known in the art, using one ring of average coil radius multiplied by the number of loops while considering coil's materials parameters.

Figure 10:
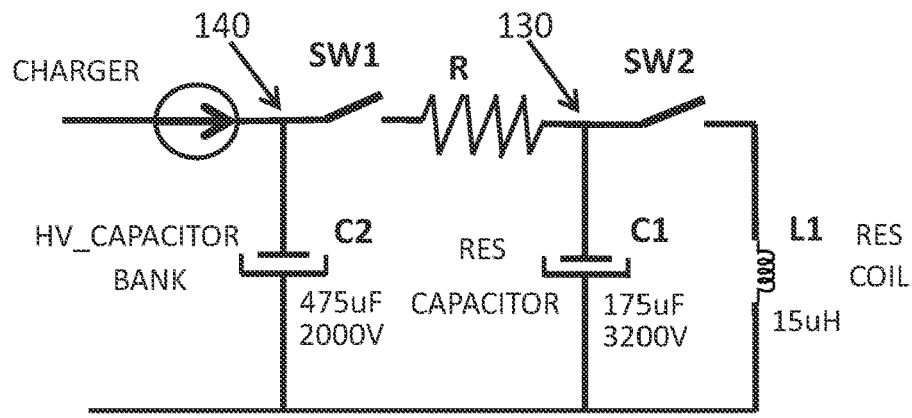
FIG. 10 schematically illustrates switched capacitors concept, according to an embodiment of the invention.
Figure 10:
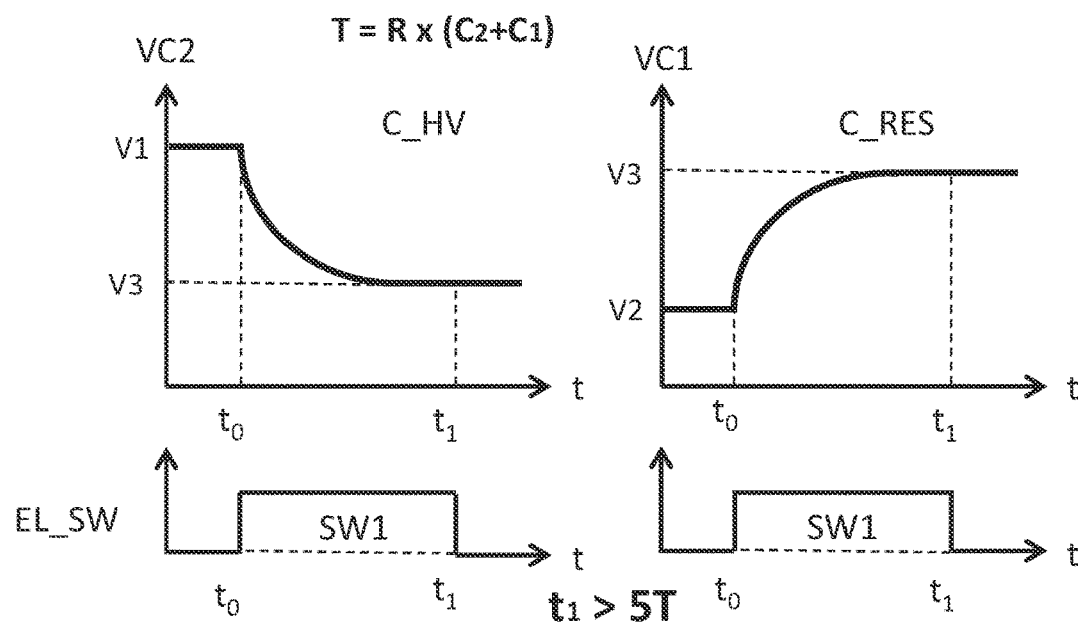
Figure 10:
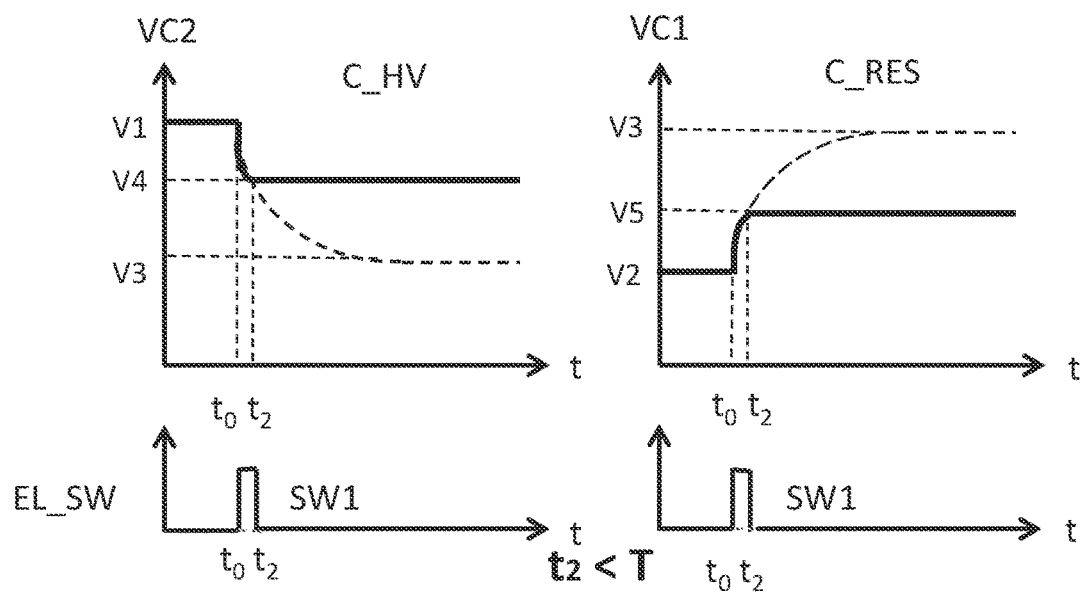

FIG. 10 schematically illustrates an embodiment that demonstrates a switched capacitor which generally resembles the configuration shown in FIG. 2 because it has MHCB, i.e., a high voltage capacitor bank C2 (475 µF/2000V), connected to a controlled HV charger, and discharge to a resonant capacitor C1 (175 µF/3200V), via switch SW1, which is controllable to discharge into the resonant coil L1 (15 µHy) when the switch SW2 is closed. C1 acts to store energy transiently during energy transfer from the capacitor bank C2 when SW1 (e.g., SW1 can be an IGBT or other suitable switching element) is closed (i.e., the closing duration of SW1 acts as a controlled duration length pulse).

In the circuit shown in FIG. 10, the charger continually supplies a charging current to the high voltage capacitor bank C2, maintaining its voltage close to a selected maximum. The resonant capacitor C1 is charged to a required level as a function of the switching duration of SW1. When the switch SW2 is closed, it allows current to flow in the resonant coil L1, thus a controllable pulse can be delivered by the closure of the switch SW2.

In the first graph, $t1>5\tau$ (a long duration pulse) in which the voltage level of C2 significantly decreases from V1 level to a much low voltage level V3. Due to such long pulse that result in a significant voltage decreasing of C2 (i.e., VC2) the voltage of C1 (i.e., VC1) increases from V2 level to the voltage level V3.

In the second graph, $t2<\tau$ (a short duration pulse) in which the voltage level of C2 slightly decreases from V1 level to a voltage level V4. Due to such short pulse the voltage of C1 (i.e., VC1) slightly increases from V2 level to the voltage level V5. The final voltage V4 is relative to the capacitive ratio between C1 and C2.

Figure 11:
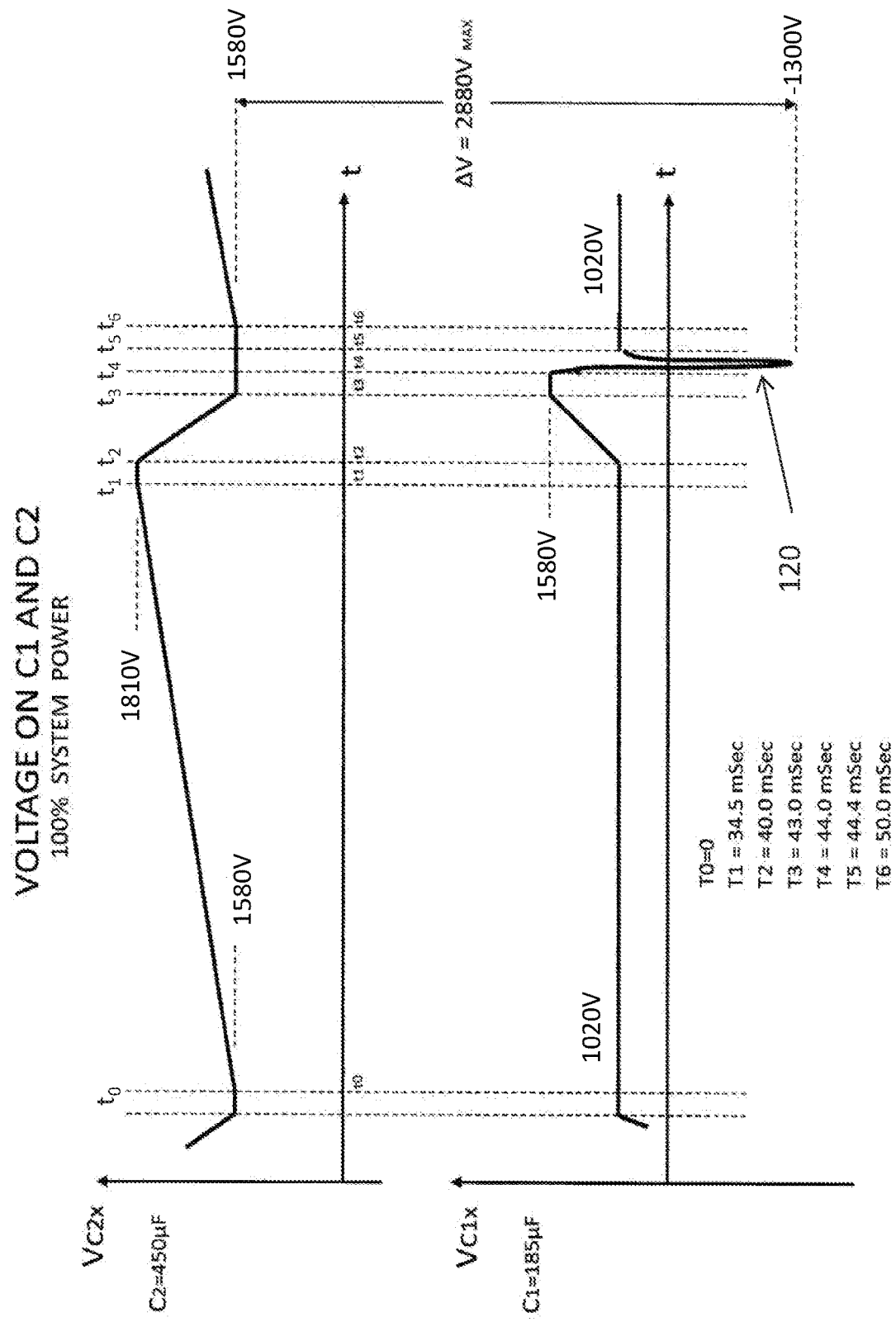
FIG. 11 is a graph that shows Voltages ver. Time of the switched capacitors concept of FIG. 10, according to an embodiment of the invention.

FIG. 11 is a graph showing voltage levels on C1 and C2 of circuit shown in FIG. 10, which indicates switched capacitors voltages vs. time. C2 charges from t0 to t1, between t2 and t3 the capacitors C1 and C2 are shorted via switch SW1, so both reach the same final voltage on t4, the SW2 is closed on t4 and a resonant pulse 120 is produced, on t6 the system starts to charge C2 again. During the resonant pulse 120 the capacitor C1 gets negative voltage peak (e.g., −1300V) with respect to the other side of SW1 on C2 (i.e., as indicated by numeral 130 in FIG. 10), and the voltage level on C2 is 1580V, which results in a differential voltage, e.g., of 2880V on SW1 (i.e., between point 130 and point 140 as indicated in FIG. 10). Such consideration must be taken when choosing the switching element SW1.

Figure 12:
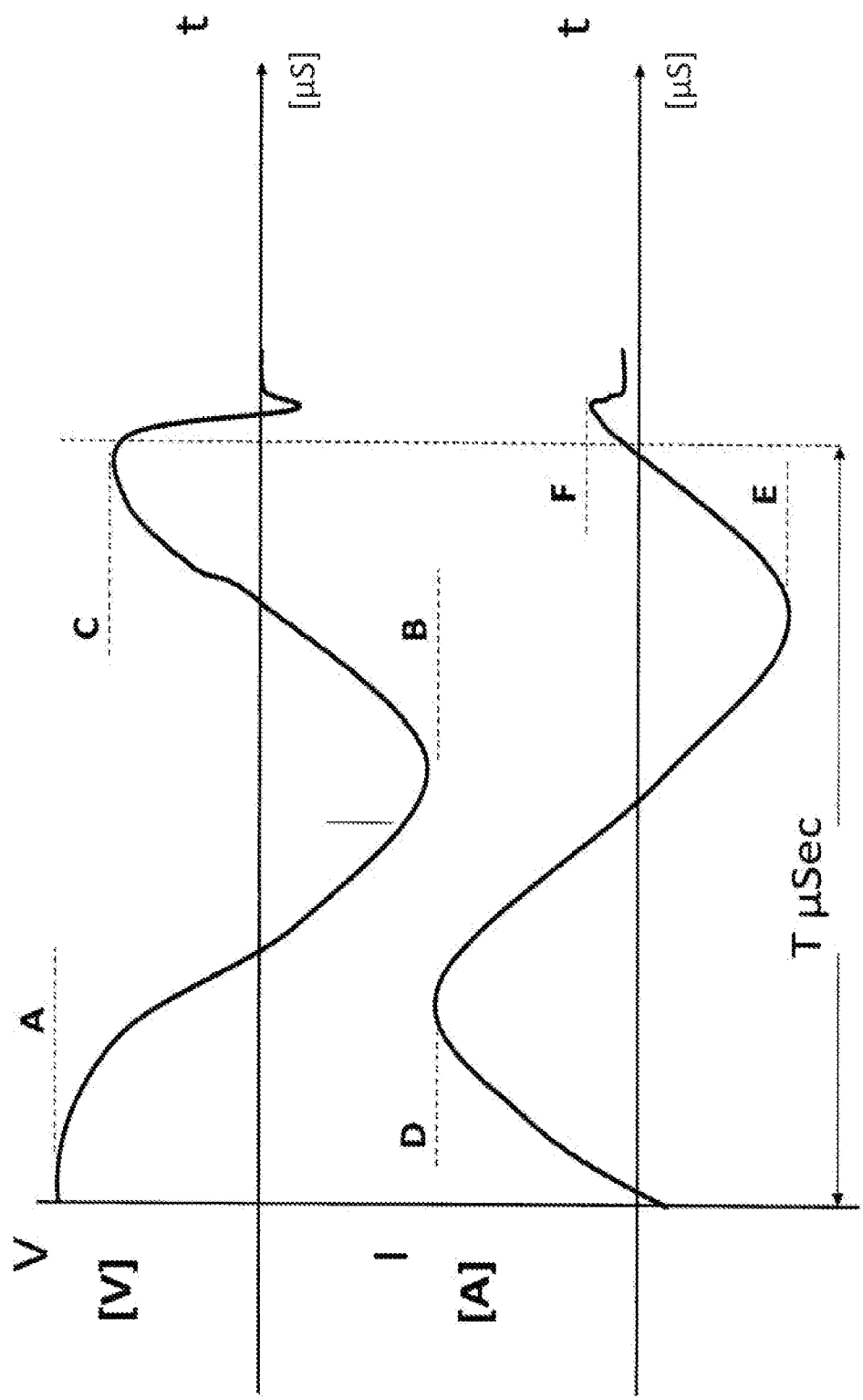
FIG. 12 is a graph that shows the resonant voltage and current of the switched capacitors concept of FIG. 10 being connected with a parallel coil such as the dual coil of FIG. 9 or any other suitable coil, according to an embodiment of the invention.

FIG. 12 is a graph showing a magnification of the resonant voltage and current of resonant pulse 120 (about the timing t4 to t5 as shown in FIG. 11). At t=0, the voltage of the capacitor C1 is the zero condition of the differential equation, and the current is zero. Closing SW2 causes the resonant pulse 120, the current acts as a sinus wave and the voltage phase is shifted in 90 degrees with the respect to the current phase (as shown in the figure).

All the above will be better understood through the following illustrative and non-limitative examples.

Figure 13:
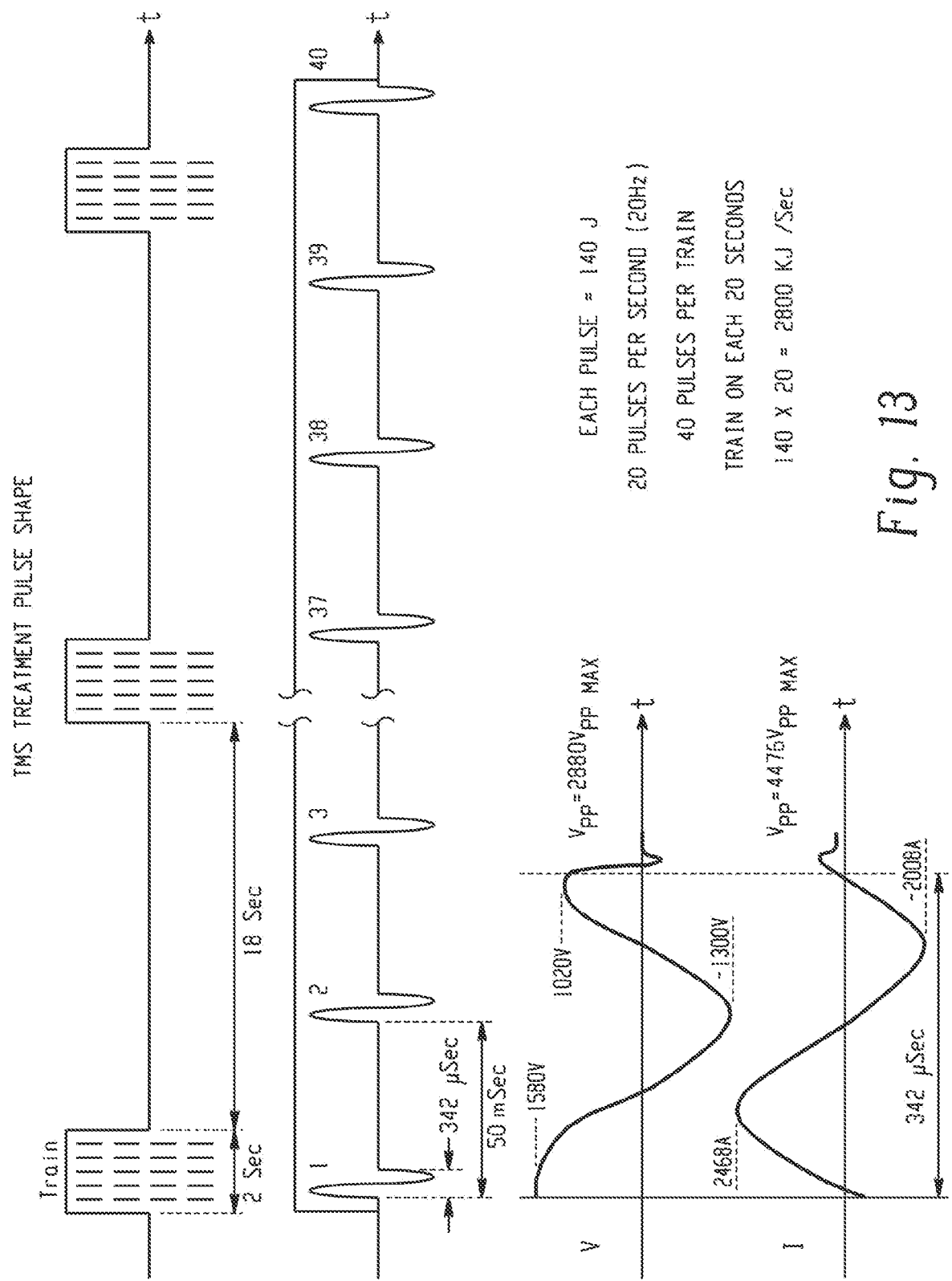
FIG. 13 schematically illustrates an example for deep TMS Brain Treatment profile per channel, according to an embodiment of the invention.

FIG. 13 shows an example of Transcranial magnetic stimulation (TMS) treatment pulse shape that can be produced by the magnetic coil driver of the present invention. In this example, each pulse is 140 joule and the system produces 20 pulses per second (20 Hz) and 40 pulses per "train", wherein the system provides "train" on each 20 seconds (2 seconds active, 18 seconds inactive), resulting in 2800 KJ/sec (i.e., 140 J×20). The uppermost graph shows the "train" on a time scale, while the graph below it shows a magnification of the 40 pulses per a single train in which the duration of each single pulse is 342 µsec, while the duration between the starting of each pulse in the train is 50 msec. The lowermost graph shows the resonant voltage and current in similar manner to FIG. 12. These graphs reflect the deep TMS treatment profile per channel (i.e., the output of each magnetic coil drive module of the present invention through which the magnetic pulses are produced and applied via the coils).

Figure 14:
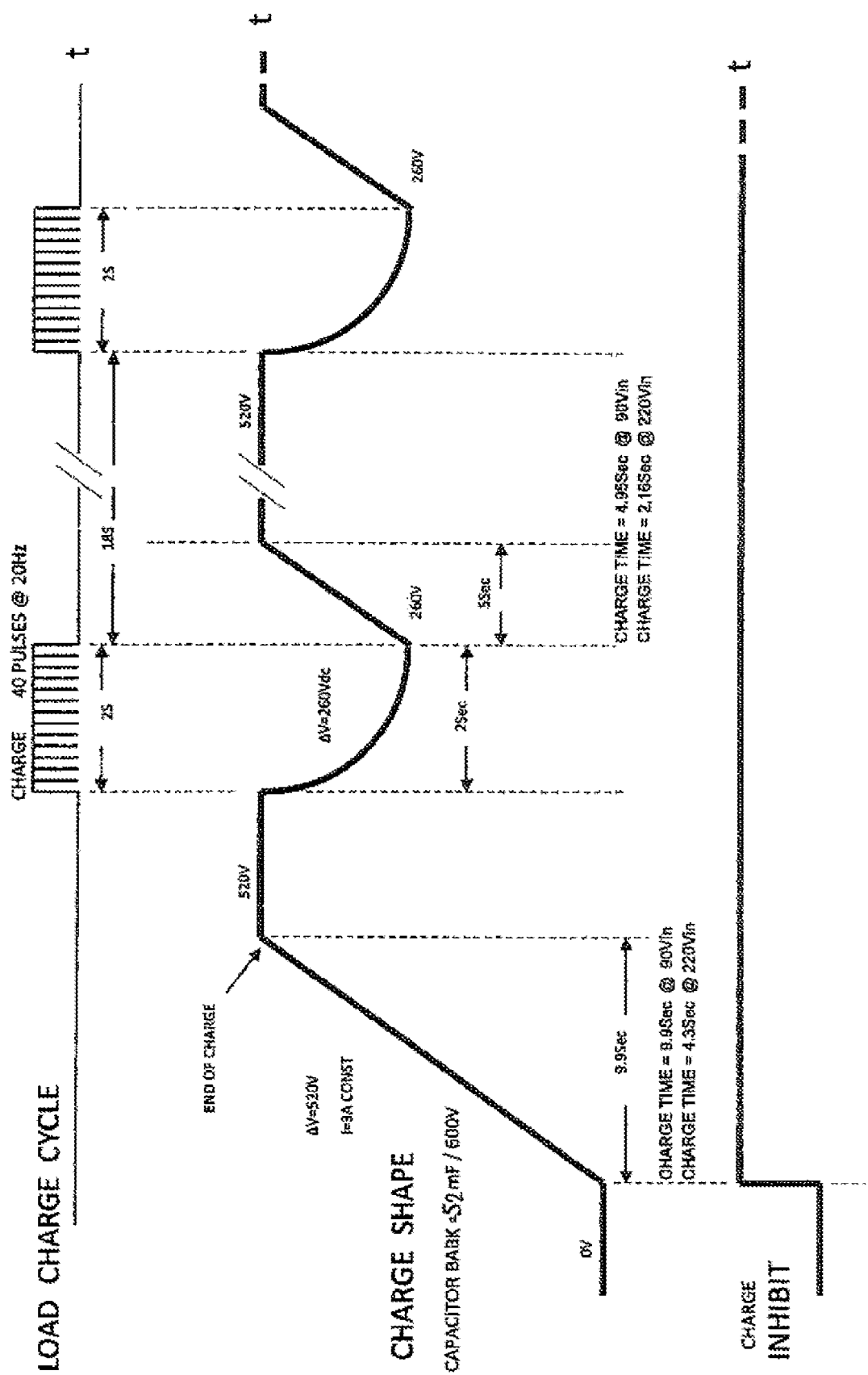
FIG. 14 schematically illustrates main charger mode of operation, according to an embodiment of the invention.

FIG. 14 is a graph showing the mode of operation of a main charger of the MCB (e.g., of a Deep TMS charge profile), according to an embodiment of the invention. At the uppermost section a load charge cycle of 40 pulses at 20 Hz is shown, in which the duration of a train of 40 pulses is 2 seconds. At the mid-section a charge shape of capacitor bank (52 mF/600V) is shown, in which the charging time from 0V to 520V takes 9.9 seconds. As shown, during the discharge of the MBC (i.e., when the pulse train of the magnetic pulses cycle are produces, in this example in a cycle of 2 seconds), the voltage drops in an exponential-like manner to 260V, and then it takes 5 more seconds to "climb" back to 520V again (i.e., charging the MBC back to 520V) when the discharge of the MBC stops by the end of the pulse train. The lowermost section shows the charge inhibit.

Figure 15:
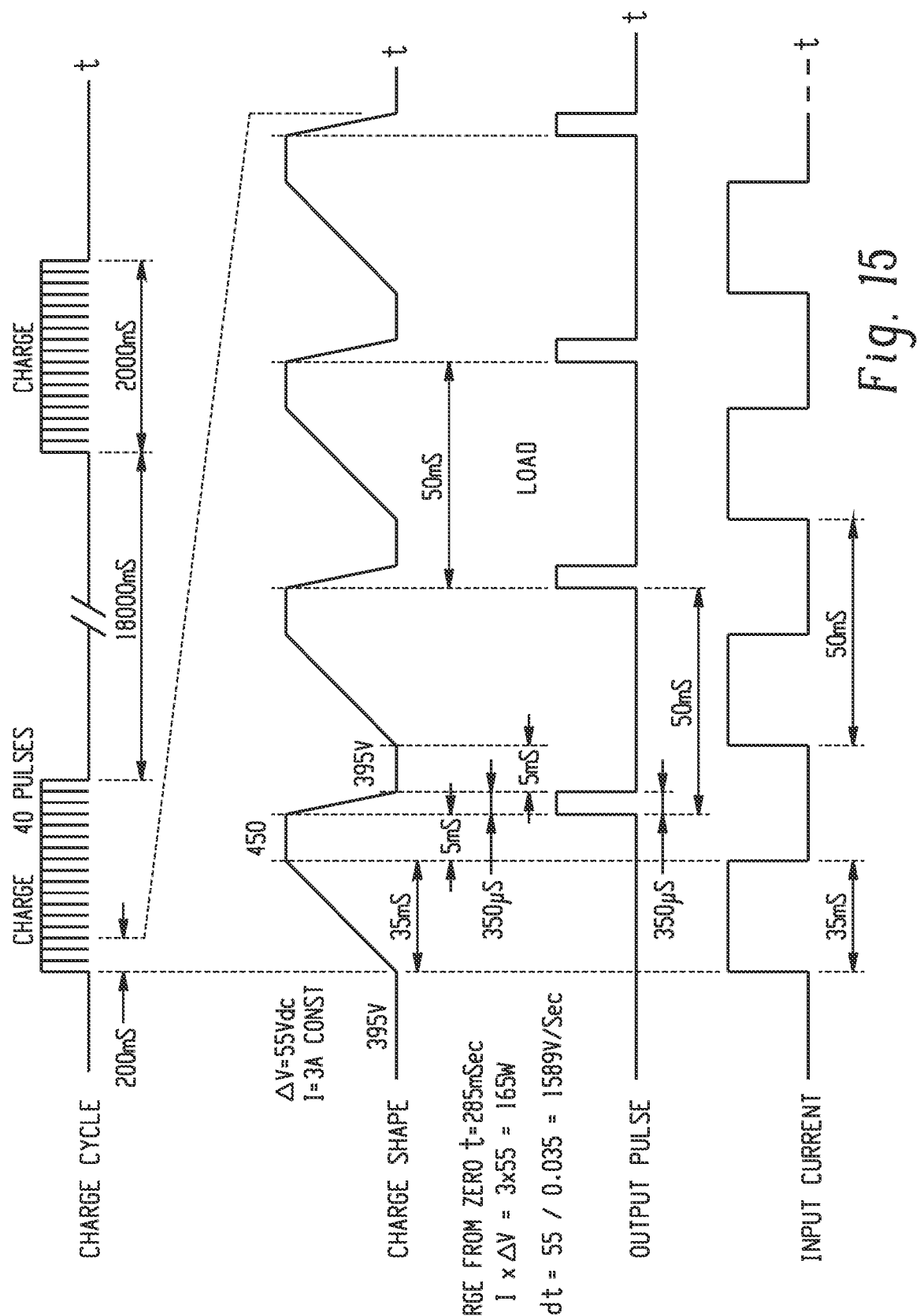
FIG. 15 schematically illustrates high-voltage (HV) chargers mode of operation of one of the channels of the magnetic coil drive module, according to an embodiment of the invention.

FIG. 15 is a graph that shows the output pulse and the behavior of the input current of single HV charger (one of four HV chargers on each magnetic drive module, e.g., as described with respect HV capacitors of FIG. 8), according to an embodiment of the invention. The single HV charger charges the corresponding HV capacitor (one of the four HV capacitors). The uppermost graph (i.e., charge cycle) shows the output pulses cycle (i.e., the pulses train). The second graph (i.e., charge shape) shows a zoom-in view the shape of the charging cycle, in which due to the constant current, the controllable duration of the charging will set the desired HV capacitor voltage. In addition, this controllable duration can be changed between pulses to another (this can be controlled by the main controller). The charging voltage of each single HV capacitor allows achieving the desired maximum voltage and capacity of the MHCB.

As aforementioned, each capacitor has its own high-voltage (HV) capacitor charger with separate charging voltage control, hence each single HV capacitor unit may be charged to a different voltage value, wherein the output of the MHCB is the sum of the voltages of all the HV capacitor units (as described hereinabove with respect to FIG. 8, in which the HV capacitor bank is comprised of 4 HV capacitor units).

Figure 16:
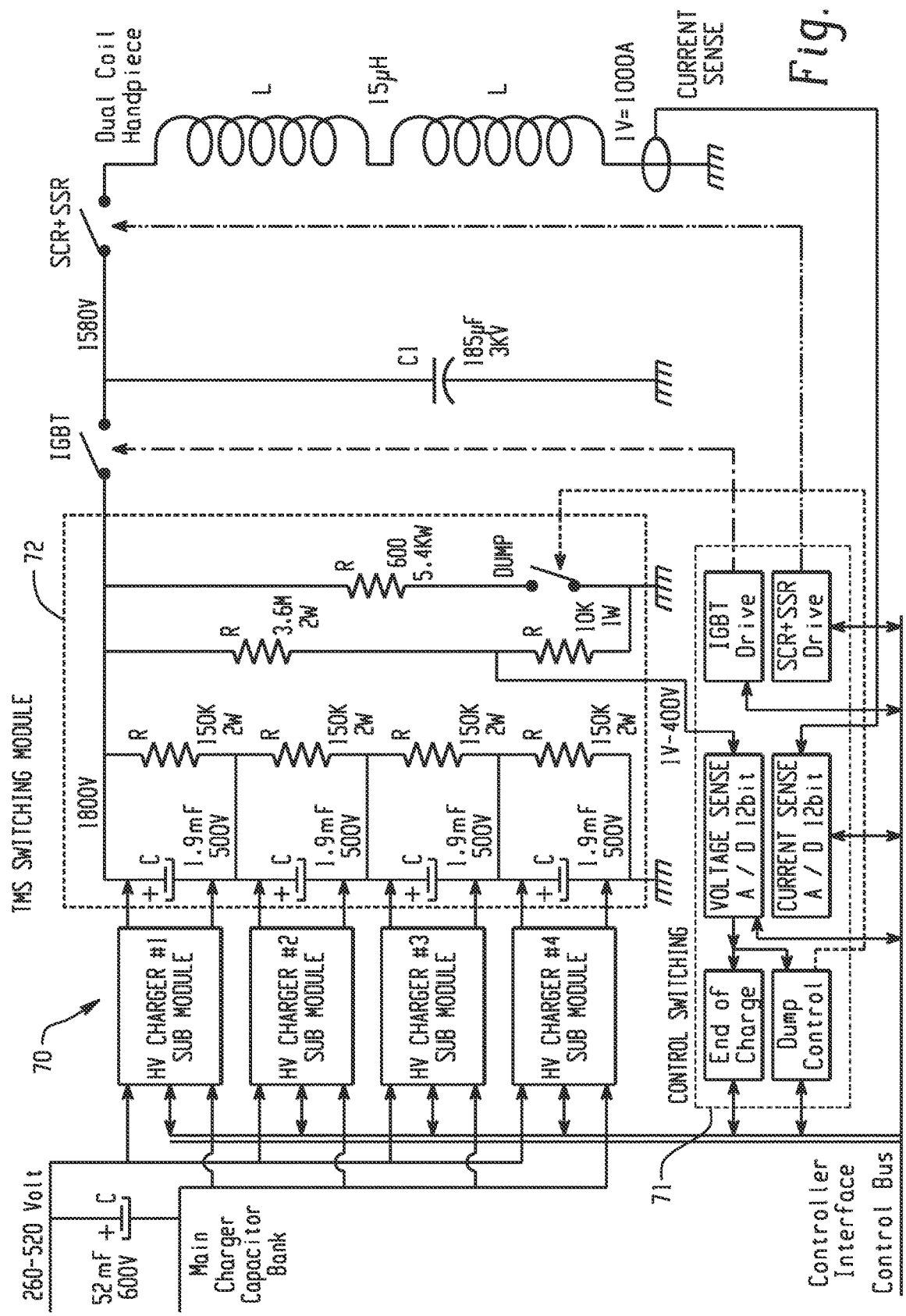
FIG. 16 schematically illustrates an implementation of TMS switching module, according to an embodiment of the invention.

FIG. 16 schematically illustrates an implementation of one channel of a magnetic TMS switching model 70, according to an embodiment of the present invention. TMS switching model 70 comprises four HV chargers #1-#4 that are being fed by a main charger capacitor bank (52 mF/600V) and have the ability to operate from 150V-600V on its input, a control switching module 71, a magnetic coil drive module 72, a dual coil hand-piece (e.g., which includes the dual coil of FIG. 9), and a voltage and current sensing arrangement for providing monitoring feedback. The switching (such as the switching concept described hereinabove with respect to SW1 and SW2 of FIG. 10) is done by an insulated-gate bipolar transistor (IGBT) which acts as SW1 and switching combinations (e.g., SCR+SSR, SCR+SCR, SCR+diode, or other switching combinations) which acts as SW2. Control switching module 71 comprises an IGBT drive for controlling the operation mode of SW1 and an SCR+SSR drive for controlling the operation mode of SW2. Control switching module 71 further comprises a voltage sense unit that is adapted to receive output voltage feedback and a current sense unit that is adapted to receive output current feedback from the dual coil hand-piece. Control switching module 71 further comprises an end of charge module and may further comprise a dump control module for operating a HV capacitor dump switch for safety aspects.

The terms, "for example", "e.g.", as used herein, are intended to be used to introduce non-limiting examples. While certain references are made to certain example system components or services, other components and services can be used as well and/or the example components can be combined into fewer components and/or divided into further components.

As will be appreciated by the skilled person the arrangement described in the figures results in a system which is capable of providing multi-channel magnetic coil drivers that enable new directions on apparatus and methods that will be based on such drivers, in particular those who may require simultaneously controlled output magnetic pulses.

It should be understood that, unless indicated otherwise, the illustrated order of operations as represented by blocks has been selected for the sake of convenience and clarity only. The order of execution of illustrated operations may be modified, or operations of the illustrated method may be executed concurrently, with equivalent results.

All the above description and examples have been given for the purpose of illustration and are not intended to limit the invention in any way. Many different mechanisms, methods of analysis, electronic and logical elements can be employed, all without exceeding the scope of the invention.

The invention claimed is:

1. An apparatus for simultaneously producing controlled magnetic pulses, wherein the apparatus is a multi-channel high power magnetic coil driver, the apparatus comprising:
a plurality of magnetic coil drive modules, each of which is connected to a combination of magnetic coils that are adapted to simultaneously produce magnetic fields in a controlled manner;
a resonant circuit that includes a capacitor and self-oscillating system with a constant cycle,
wherein a signal of a magnetic stimulation in the form of a sinusoidal wave as applied by the magnetic coils is a solution of a differential equation of the resonant circuit; and
a main controller, wherein each magnetic pulse can change current values by the main controller as results of feedback of a previous magnetic pulse, thereby enabling an output of the multi-channel high power magnetic coil driver to act as a regulated output that delivers magnetic energy that is controlled by the feedback, wherein each magnetic coil drive module outputs current and voltage and wherein the output current and voltage of each magnetic coil drive module are controlled by changing an initial condition of the differential equation by a change of a controlled voltage that charges the capacitor of the resonant circuit before each produced magnetic pulse.

2. The apparatus according to claim 1, in which each channel of the magnetic coil driver is adapted to work simultaneously and controlled by the main controller, while enabling each channel of the magnetic coil driver to work according to a different set of parameters, wherein each channel of the magnetic coil driver can deliver a different magnetic energy.

3. The apparatus according to claim 2, in which the main controller is configured to receive a monitoring feedback from each magnetic coil drive module.

4. The apparatus according to claim 1, in which each magnetic coil drive module is powered by one or more capacitor banks.

5. The apparatus according to claim 4, in which the one or more capacitor banks are being charged by a charger that is being fed by a power source.

6. The apparatus according to claim 1, in which each of the magnetic coils is assembled from a single magnetic coil or from a plurality of magnetic coils that are connected in serial, parallel or any other combination.

7. The apparatus according to claim 1, in which the combination of magnetic coils that are connected to each magnetic coil drive module is selected from the group consisting of an air coil, Tesla coil, electromagnet coil, or any other type of magnetic coils or inductors that can be connected in serial or parallel or a combination of both.

8. The apparatus according to claim 3, in which each magnetic coil drive module comprises an internal high voltage capacitor bank that is charged according to a set of parameters provided by the main controller and power calculation by a local control from a voltage and current feedback from the magnetic coils of the magnetic coil drive module, wherein a voltage charged to an oscillating output capacitor from the internal high voltage capacitor bank may be changed for each pulse on an output train pulse, and the output current and voltage of each magnetic coil drive modules, is sampled and sent to the main controller as the monitoring feedback.

9. The apparatus according to claim 1, wherein the apparatus is a multi-channel deep Transcranial Magnetic Stimulations (TMS) brain stimulation apparatus.

10. The apparatus according to claim 1, wherein each magnetic coil drive module comprises a transmitting coil that is adapted to wirelessly produce the controlled magnetic pulses that are suitable to be received by a corresponding receiving coil.

11. The apparatus according to claim 1, wherein the multi-channel high power magnetic coil driver forms an anti-gravity plate in which the magnetic coils are deployed at a bottom of a platform in such a way that the magnetic pulses produce force vectors towards a surface beneath the platform, wherein the magnetic coils are configured to work in an alternating manner, and the magnetic coils comprise a first set of magnetic coils and a second set of magnetic coils, and when the first set of the magnetic coils are active and produce the magnetic pulses, the second set of the magnetic coils are inactive.

12. A method for simultaneously producing controlled magnetic pulses, the method comprising:
    providing a plurality of magnetic coil drive modules, each of which is connected to a combination of magnetic coils that are adapted to simultaneously produce magnetic fields in a controlled manner, and a resonant circuit that includes a capacitor and a self-oscillating system with a constant cycle,
    wherein a signal of a magnetic stimulation in the form of a sinusoidal wave is applied by the magnetic coils and the signal is a solution of a differential equation of a resonant circuit;
    providing a main controller, wherein each magnetic pulse can change values by the main controller as results of feedback of a previous magnetic pulse;
    providing an output of a multi-channel high power magnetic coil driver to act as a regulated output that delivers magnetic energy that is controlled by the feedback,
    wherein each magnetic coil drive module outputs current and voltage, and the method further comprises controlling the output current and voltage of each magnetic coil drive module by changing an initial condition of the differential equation by a change of a controlled voltage that charges the capacitor of the resonant circuit before each produced magnetic pulse.

* * * * *